United States Patent
Schoeb

(10) Patent No.: US 10,389,207 B2
(45) Date of Patent: Aug. 20, 2019

(54) ROTATIONAL MACHINE AS WELL AS APPARATUS HAVING A ROTATIONAL MACHINE

(75) Inventor: Reto Schoeb, Rudolfstetten (CH)

(73) Assignee: LEVITRONIX GMBH, Zurich (CH)

( * ) Notice: Subject to any disclaimer, the term of this patent is extended or adjusted under 35 U.S.C. 154(b) by 244 days.

(21) Appl. No.: 14/119,166

(22) PCT Filed: May 16, 2012

(86) PCT No.: PCT/EP2012/059169
§ 371 (c)(1),
(2), (4) Date: Nov. 20, 2013

(87) PCT Pub. No.: WO2012/159966
PCT Pub. Date: Nov. 29, 2012

(65) Prior Publication Data
US 2014/0062239 A1    Mar. 6, 2014

(30) Foreign Application Priority Data

May 20, 2011 (EP) ..................................... 11166923

(51) Int. Cl.
| | |
|---|---|
| A61M 1/10 | (2006.01) |
| A61M 1/12 | (2006.01) |
| H02K 7/09 | (2006.01) |
| B01F 13/08 | (2006.01) |
| F16C 32/04 | (2006.01) |
| H02K 29/08 | (2006.01) |

(52) U.S. Cl.
CPC .............. H02K 7/09 (2013.01); A61M 1/1015 (2014.02); B01F 13/0872 (2013.01);
(Continued)

(58) Field of Classification Search
CPC ....... H02K 7/09; H02K 29/08; A61M 1/1015; F16C 32/0461; F16C 32/0497
(Continued)

(56) References Cited

U.S. PATENT DOCUMENTS 3,079,518 A * 2/1963 Moore ................. H02K 16/025
 310/115
3,447,842 A * 6/1969 Steingroever ....... F16C 32/0408
 310/90
(Continued)

FOREIGN PATENT DOCUMENTS

| | | |
|---|---|---|
| EP | 0 900 572 A1 | 3/1999 |
| WO | 2011/024470 A2 | 3/2011 |
| WO | WO 2011024470 * | 3/2011 |

OTHER PUBLICATIONS

English translation of Liao (CN 101030714); Sep. 2007; China.*

*Primary Examiner* — Bernard Rojas
*Assistant Examiner* — Ahmed Elnakib
(74) *Attorney, Agent, or Firm* — Kilpatrick Townsend & Stockton LLP

(57) ABSTRACT

A rotational machine, designed as a bearing free motor, including a stator designed as a bearing and drive stator having a stator winding and a disc-shaped rotor stored magnetically contact free within the stator. An axial height (H) of the rotor is smaller than or equal to a half diameter (D) of the rotor and with the rotor being passively stabilized by reluctance forces with regard to the stator both against a displacement along a rotational axis (A) of the rotor and also against a tilting from an equilibrium position (G), and with the stator including a permanent magnet for the generation of a homopolar magnetic flux (HΦ). The rotor is a ring-like rotor rotatably arranged about a pole piece of the stator and the rotor includes a ferromagnetic material (FM) and no permanent magnet.

17 Claims, 15 Drawing Sheets

Figure 1A:
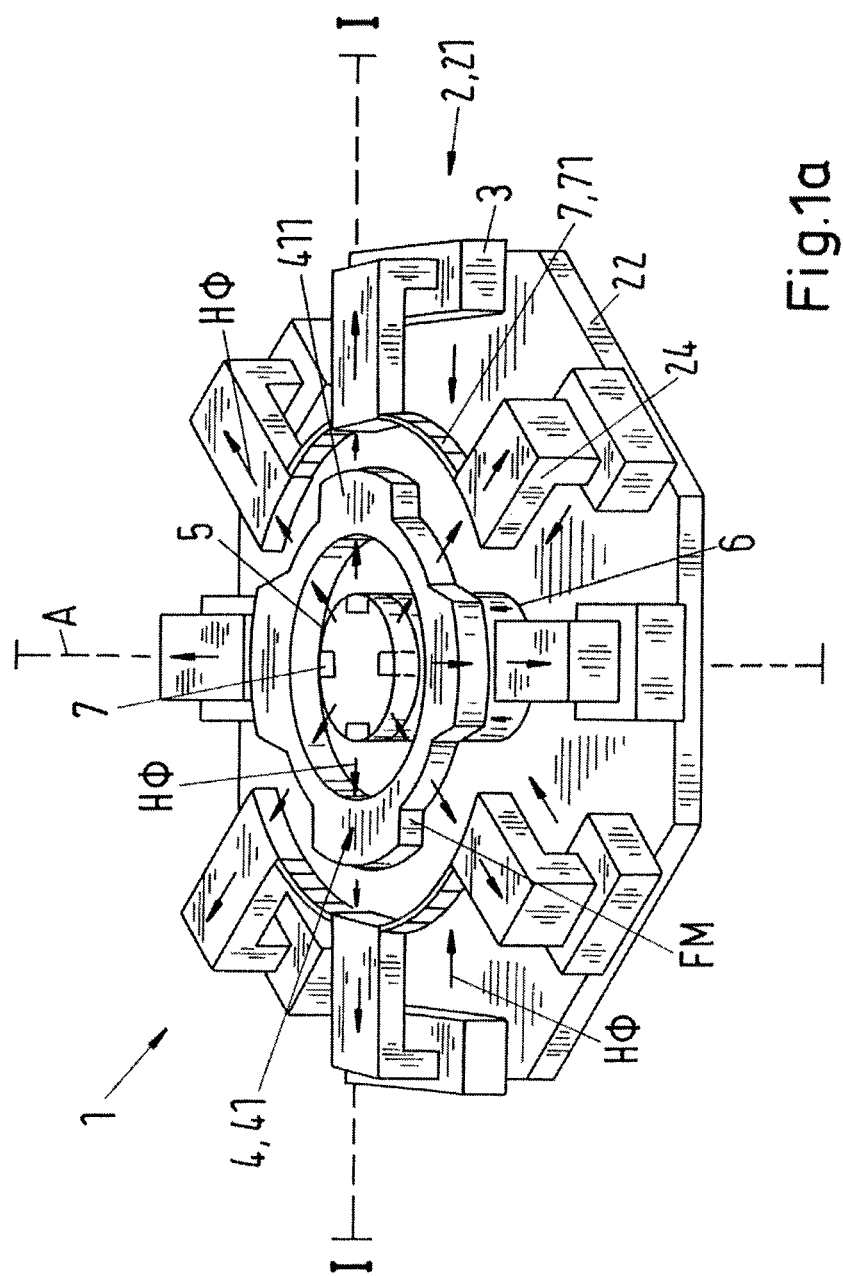

(52) U.S. Cl.
CPC ...... *F16C 32/0461* (2013.01); *F16C 32/0497* (2013.01); *H02K 29/08* (2013.01); *A61M 1/101* (2013.01); *A61M 1/1031* (2014.02); *A61M 1/1086* (2013.01); *A61M 1/12* (2013.01); *F16C 2360/44* (2013.01)

(58) Field of Classification Search
USPC ....... 310/90.5, 178, 68 R, 68 E, 62, 63, 119, 310/103, 102 A, 266, 112; 417/423; 415/900
See application file for complete search history.

(56) References Cited

U.S. PATENT DOCUMENTS

| | | | | |
|---|---|---|---|---|
| 3,549,923 | A * | 12/1970 | Kurakin | H02K 19/103 310/154.04 |
| 3,689,787 | A * | 9/1972 | Simon Saretzky | H02K 37/20 310/266 |
| 5,470,208 | A * | 11/1995 | Kletschka | F04D 5/001 415/900 |
| 5,863,179 | A | 1/1999 | Westphal et al. | |
| 6,053,705 | A * | 4/2000 | Schob | A61M 1/101 417/356 |
| 6,171,078 | B1 | 1/2001 | Schöb | |
| 7,112,903 | B1 * | 9/2006 | Schob | F16C 32/0465 310/90.5 |
| 7,416,525 | B2 * | 8/2008 | Wampler | F04D 29/047 600/16 |
| 2005/0151437 | A1 | 7/2005 | Ramu | |
| 2009/0121571 | A1 | 5/2009 | Onuma | |
| 2012/0156071 | A1 * | 6/2012 | Hijikata | A61M 1/101 417/423.12 |
| 2017/0040868 | A1 * | 2/2017 | Noh | H02K 7/09 |

* cited by examiner

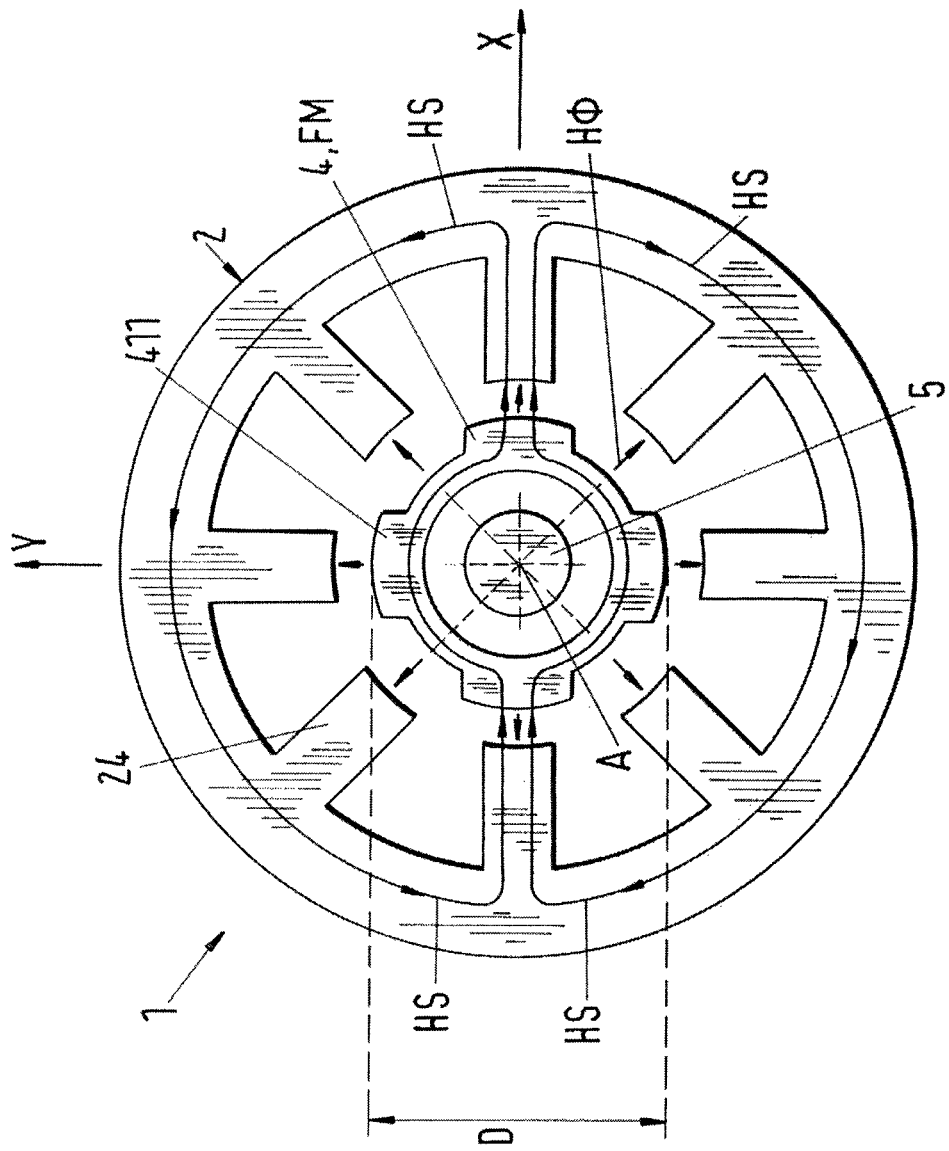

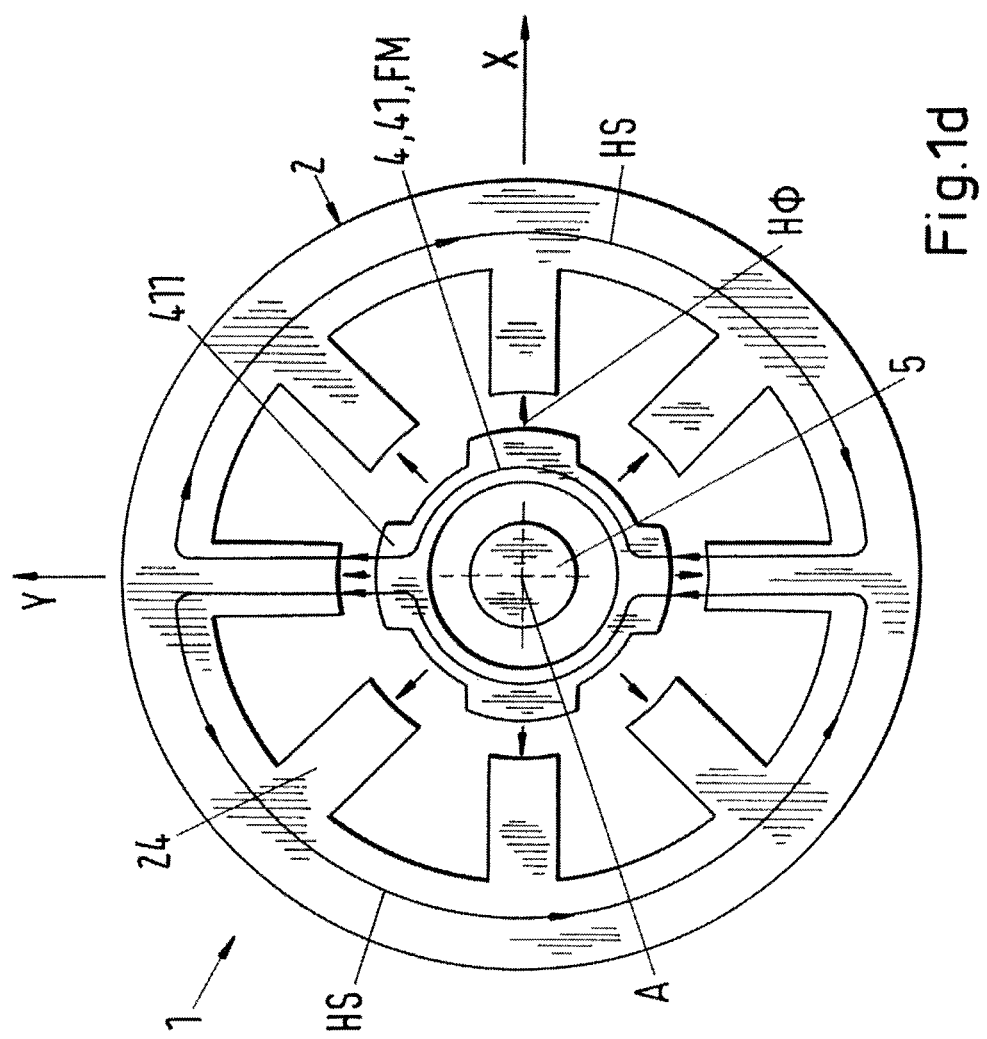

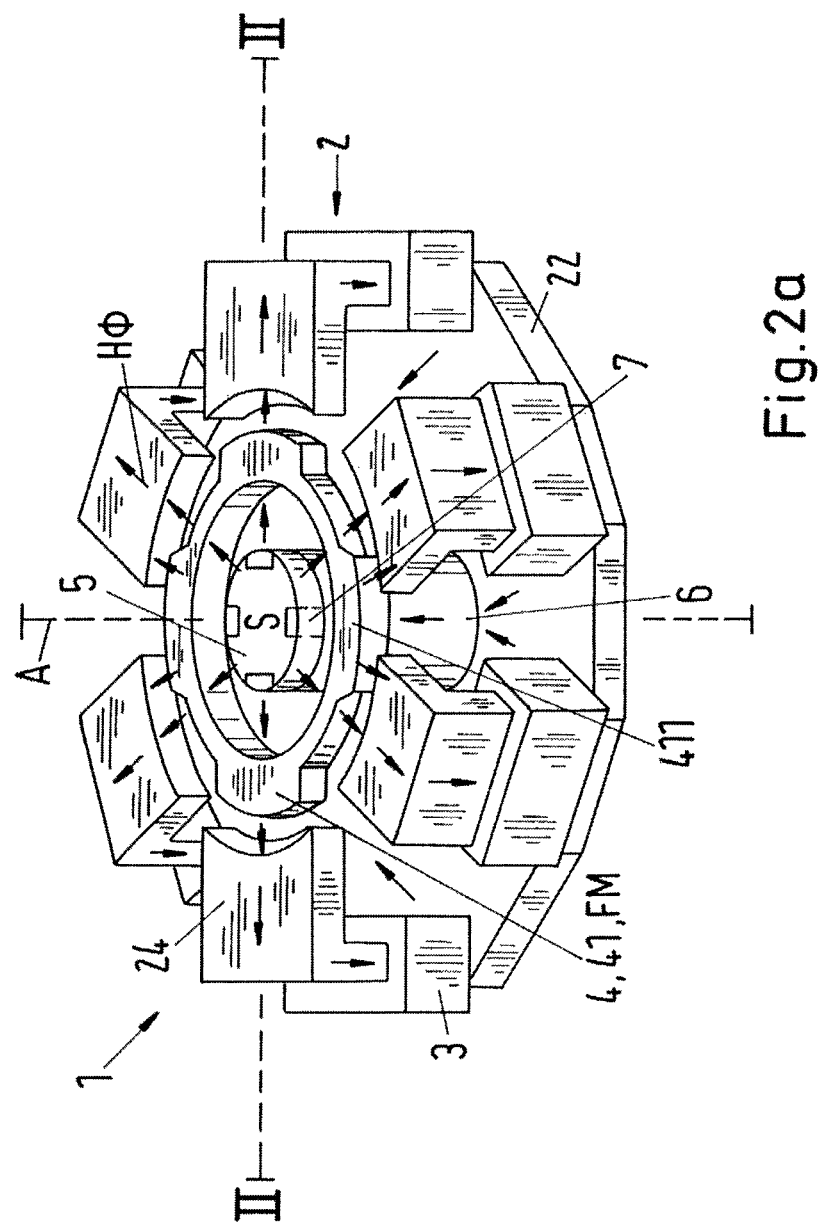

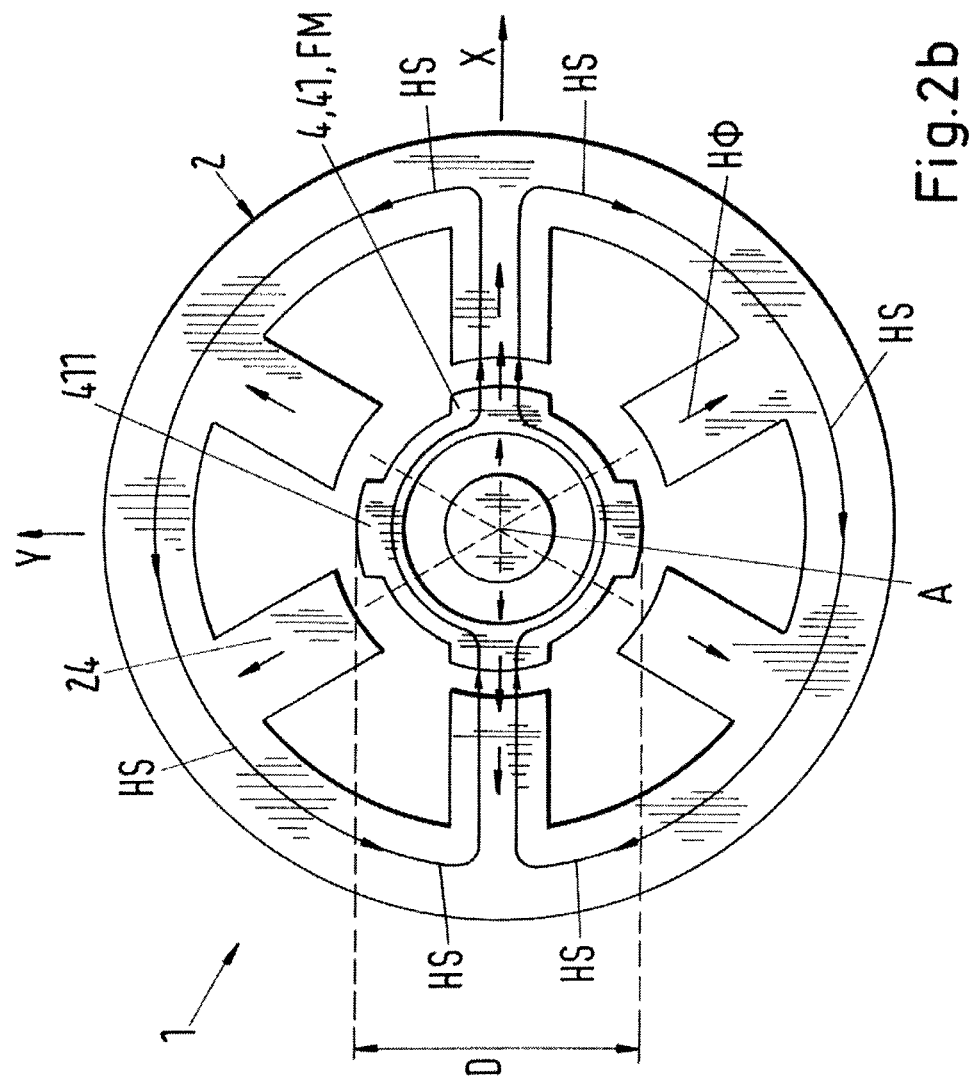

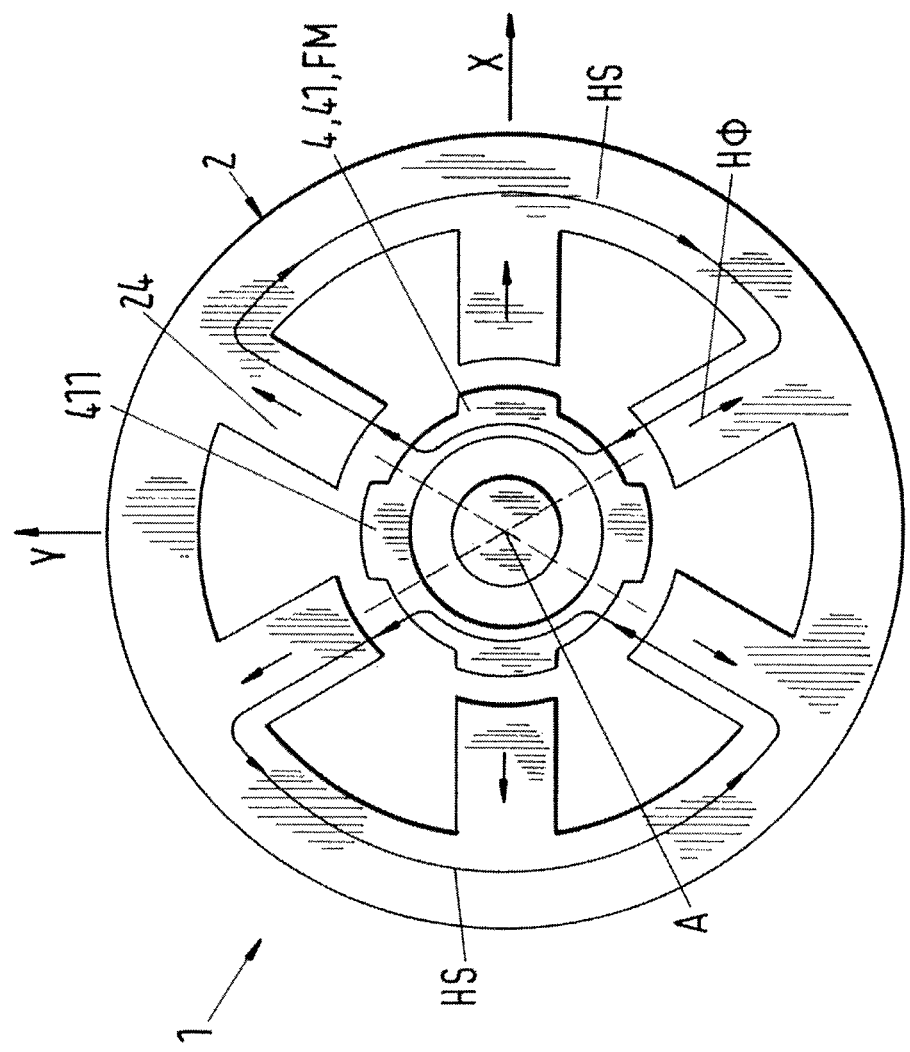

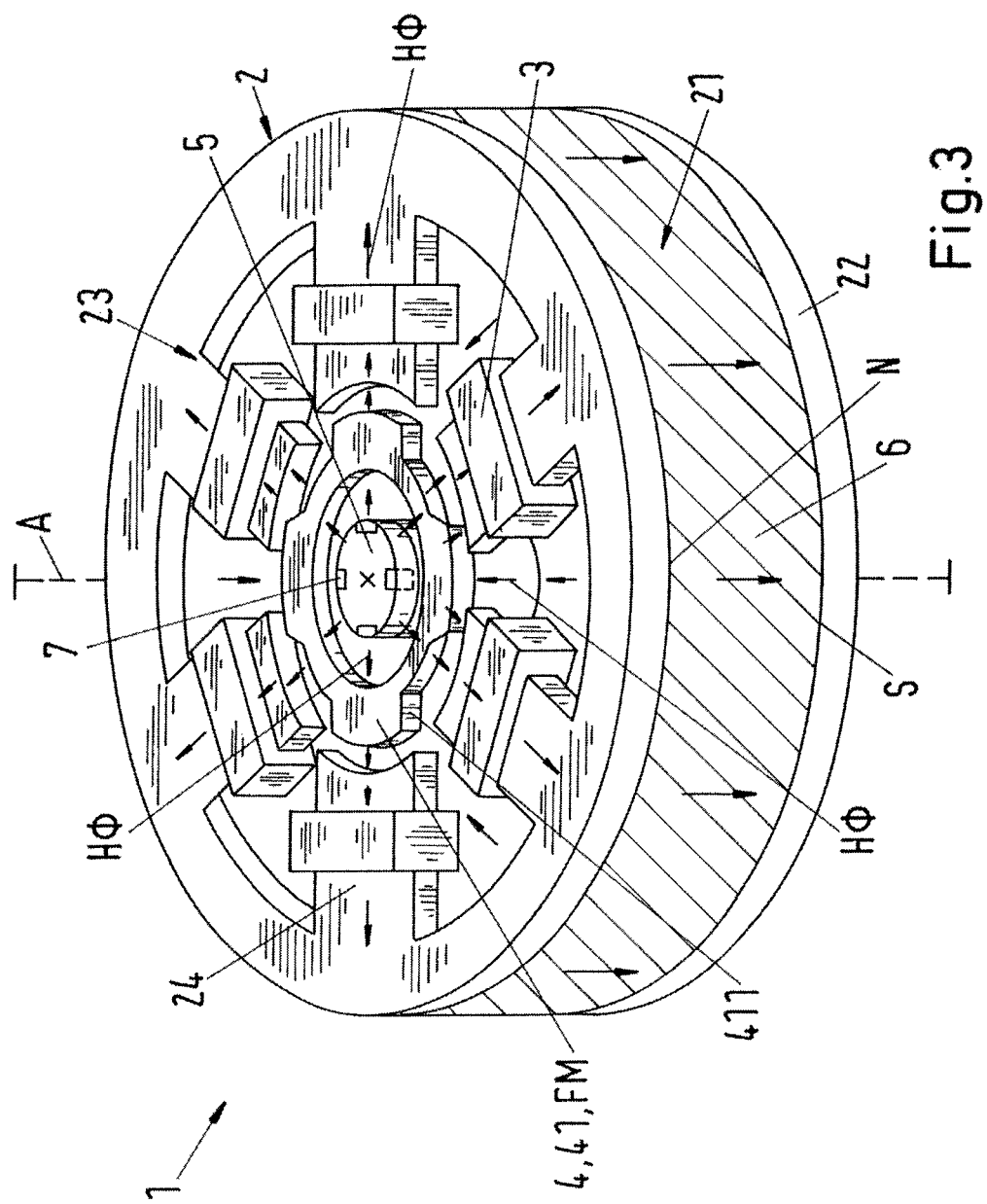

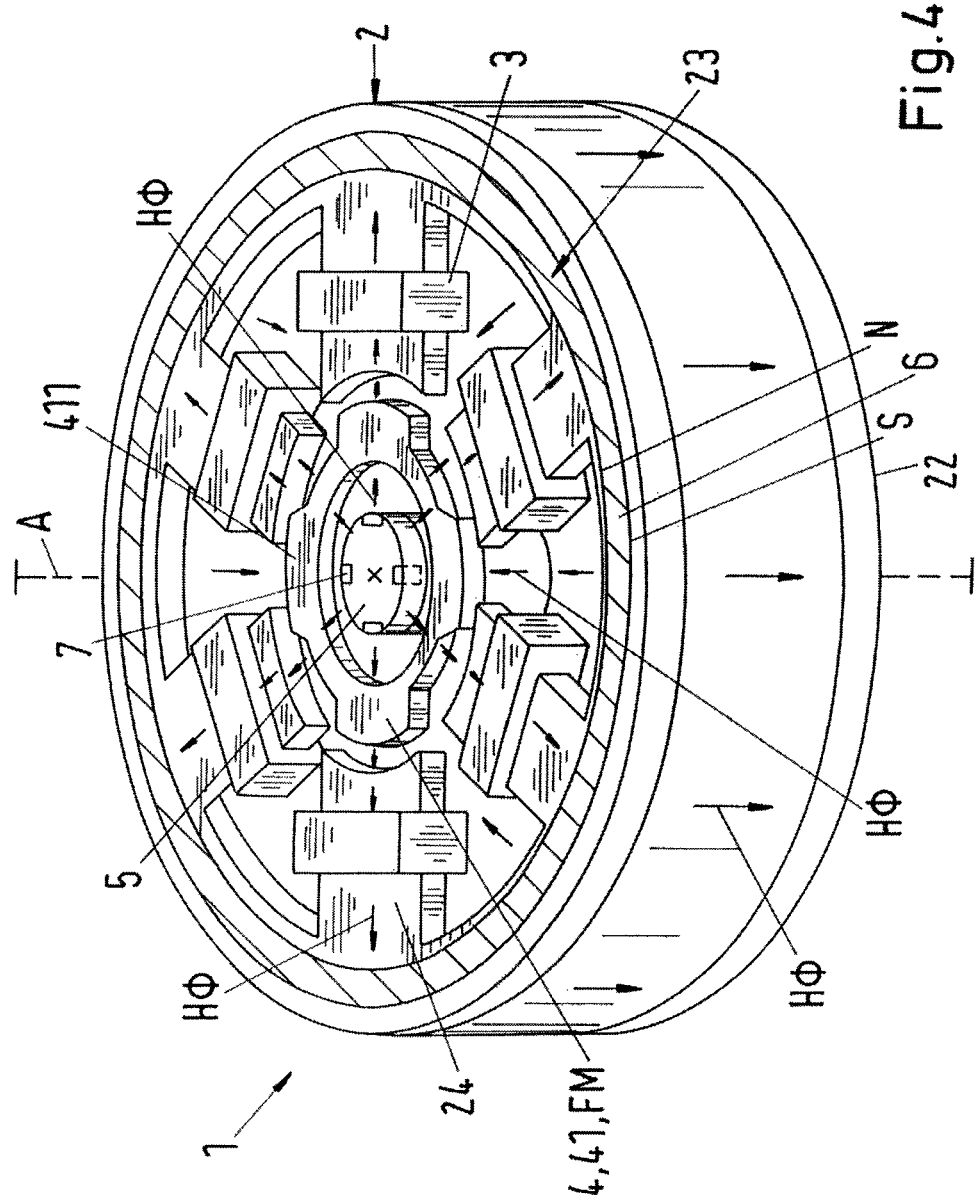

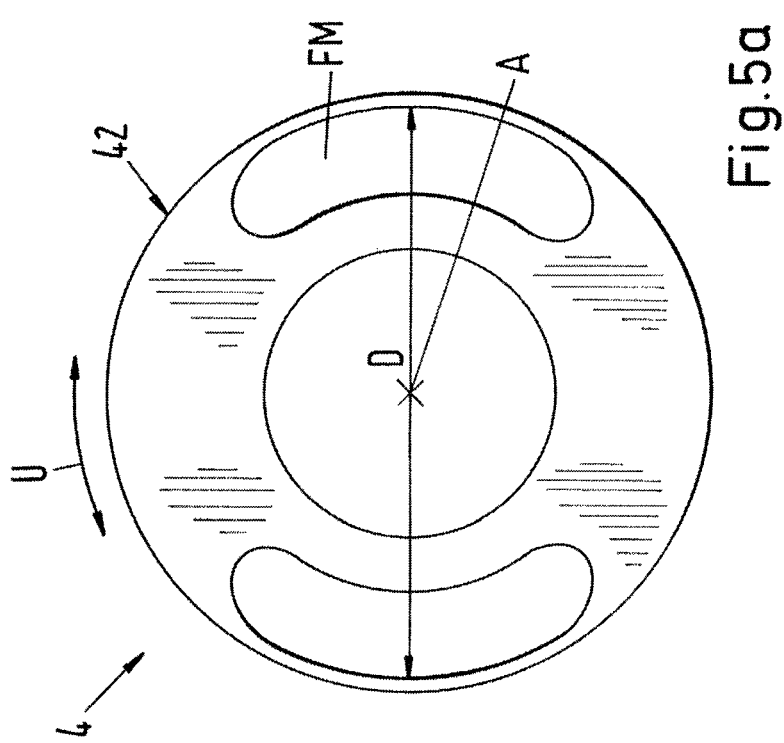

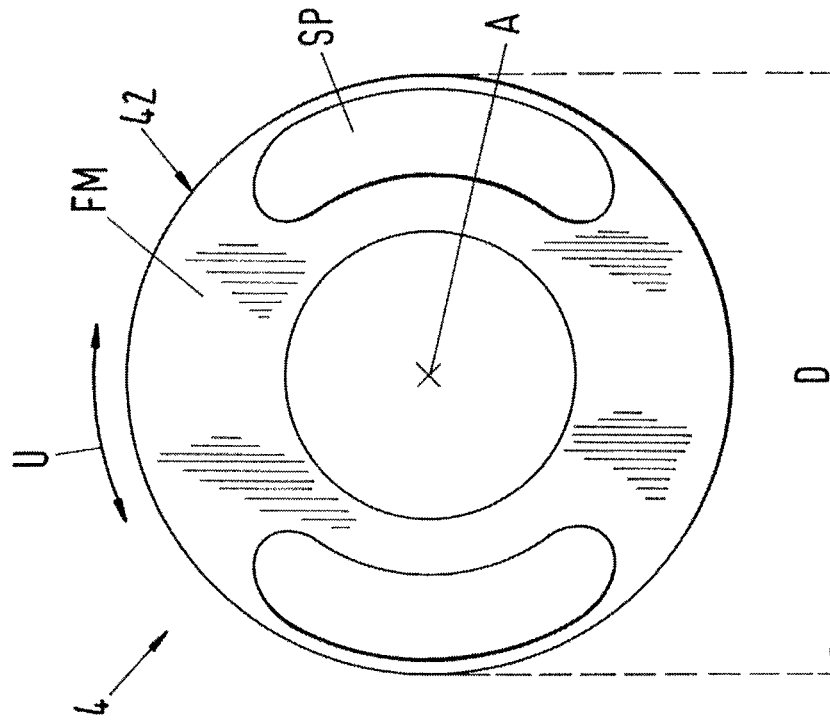

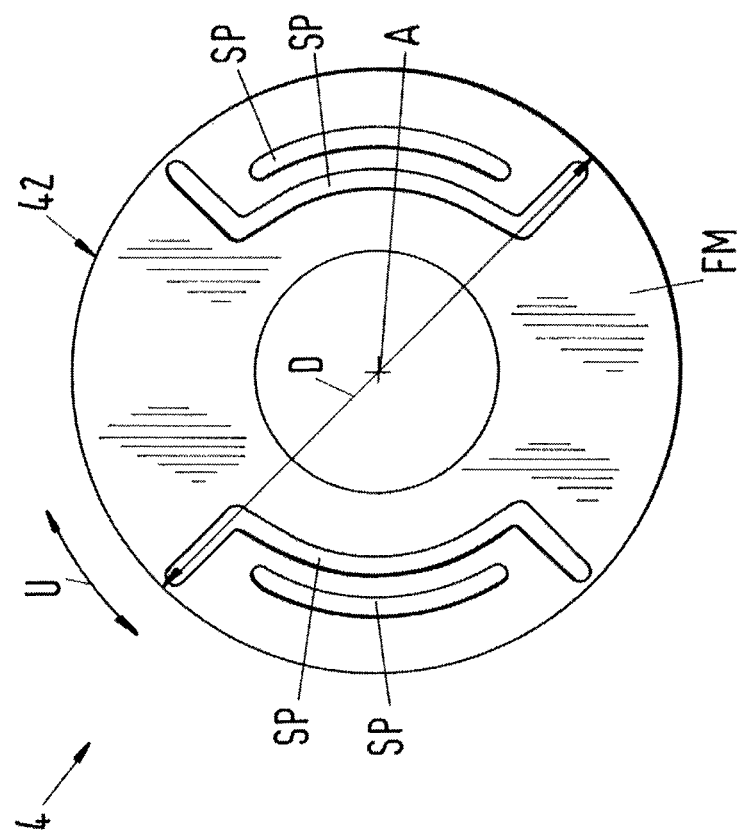

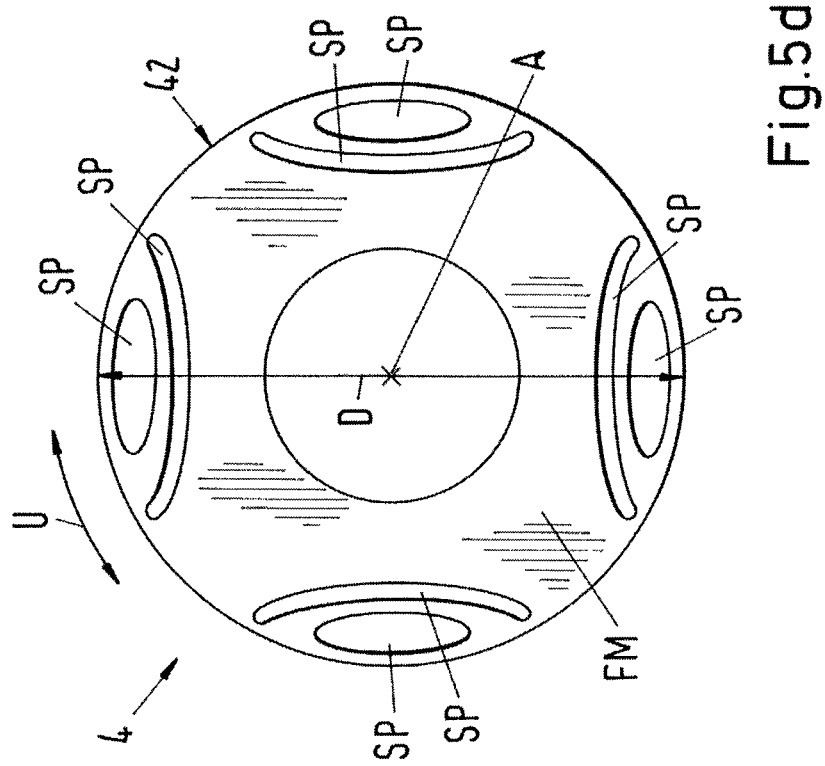

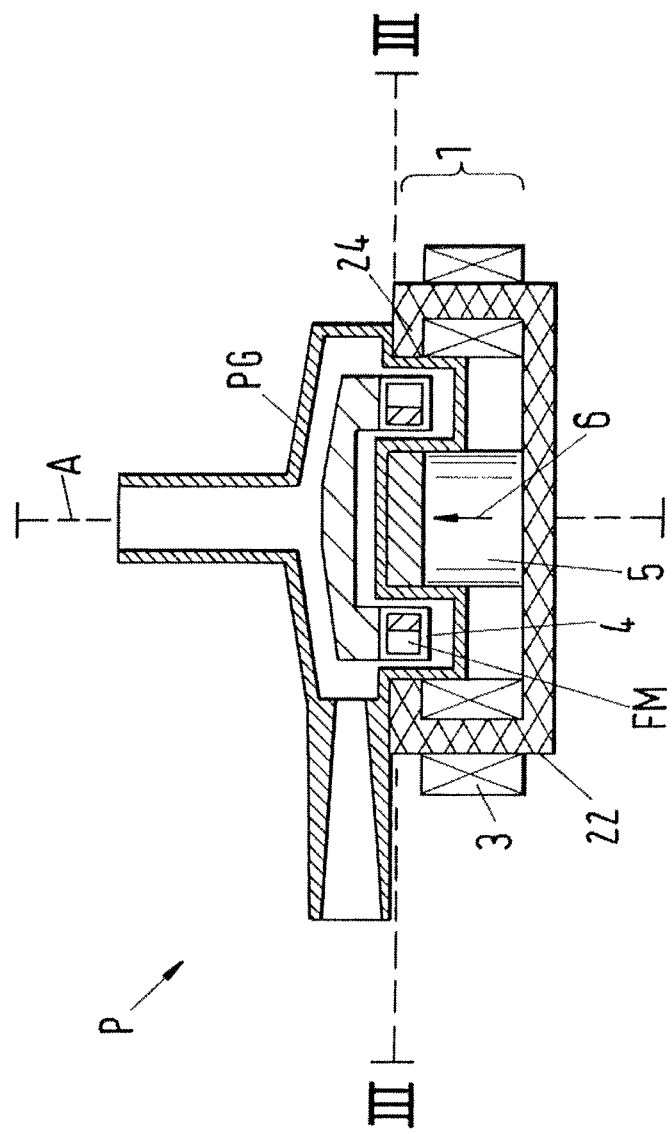

ROTATIONAL MACHINE AS WELL AS APPARATUS HAVING A ROTATIONAL MACHINE

This application is a National Stage of International Application No. PCT/EP2012/059169 filed May 16, 2012, and which claims the benefit of European Patent Application No. 11166923.0 filed May 20, 2011, the disclosures of which are incorporated herein by reference.

The invention relates to a rotational machine designed as a bearing-free motor, to a rotor for such a rotational machine, as well as to an apparatus having a rotational machine designed as a bearing-free motor, in particular to a wafer machining plant, a bio-reactor plant, a pump or a mixer or any other processing plant having a rotational machine in accordance with the preamble of the independent claims 1 and 15.

Rotational machines which are adapted as so-called bearing-free motors have been established as a rotary drive for different units and applications for a long time in the prior art. Such bearing-free motors having a stator designed as a bearing and drive stator and having a rotor stored magnetically contact-free within the stator and which are used because of their specific advantages, namely in particular because of their stable running properties and the omission of any mechanical bearing at the rotor, in particular in many special cases of application as pumps or dosage units, for example in the semiconductor industry for the handling of mechanically aggressive liquids such as slurry. Amongst others things, such a rotary drive is described in EP 1 063 753.

A different classical field of application of such bearing-free motors is the treatment of sensitive or highly pure liquids. In this respect the technology of the bearing-free motors is, for example, used very advantageously in blood pumps or in bio-reactors, or for handling highly sensitive and/or highly pure liquids in the pharmaceutical and chemical industry, as well as generally in the medical field and/or in the field of medical technology.

The power generation for the magnetic storage of known bearing-free motors in disc-running adaptation in this respect only occurs in one plane, namely in the plane of the rotor. The rotor is actively stabilized in this plane in both radial directions, wherein the stabilization in the axial direction and the stabilization with regard to the tilting gradient of the known motors takes place purely passively by reluctance forces.

A known bearing-free motor which, amongst other things, should be improved by the present invention is, for example, disclosed in WO-A-96/31934 or in a different variant also in EP-A-0 900 572 and the principle of such bearing-free motors to which the present invention, amongst other things, relates should be explained in more detail in the following for a better understanding.

The term bearing-free motor is used in the scope of this application to mean that the motor is completely magnetically stored, wherein no separate mechanical bearings are provided. For this purpose, the stator is designed as a bearing and drive stator; it is therefore both a stator of the electric drive and also a stator of the magnetic storage. For this purpose the winding of the stator includes a drive winding and a control winding which in principle can be provided anywhere at the stator in particular at one and the same stator tooth or in different examples also on separate stator teeth, wherein, in particular for modern bearing-free motors also a single electric winding can simultaneously serve as a drive and control winding. A magnetic rotary field can be generated by means of the electric windings which, on the one hand, exert a torque onto the rotor causing its rotation and which, on the other hand, exerts an arbitrary settable transverse force onto the rotor, so that its radial position is actively controllable and/or regulatable. Only when the rotor is designed as a disc-shaped rotor or as a ring-shaped rotor is a passive magnetic storage with stabilization against tiling possible via reluctance forces.

Thus three degrees of freedom of the rotor are actively regulatable. With regard to three further degrees of freedom, namely its axial displacement in the direction of the rotary axis and to tilting with regard to the plane perpendicular to the rotary axis (two degrees of freedom) the rotor is passively magnetically stabilized, this means it is not actively controllable, but magnetically stabilized by reluctance forces.

So that the axial push, which is caused, for example, by the pressure difference present between the inlet and the outlet in a pump, does not frequently have to be absorbed by the axial bearings, many different measures are known in centrifugal pumps to balance out the rotor with regard to the axial direction.

The problem of the axial push balance can thus become particularly grave for pumps with magnetically stored rotors, in particular when the axial storage takes place completely magnetically via reluctance forces without mechanical bearings. Beside the magnetic reluctance forces only constructive measures are available with regard to the balancing out of the rotor of such a bearing-free motor which influence the axial position via fluid dynamic balancing forces.

The problems associated therewith have in the meantime be solved to a large extent by the applicant in accordance with PCT/EP2010/062789, so that the measures described there can also be used very advantageously for the construction of apparatuses using a rotational machine of the present invention.

Apart from this, the prior art bearing-free motors are known in many different embodiments.

For example, WO-A-96/31934 discloses e.g. a pump having a so-called temple motor, in which the coil cores of a stator each have the shape of an "L", wherein one of the shanks respectively runs parallel to the axis of rotation, while the other shank is directed radially inward towards the axis of rotation. The stator, which is designed as a bearing and drive stator, preferably has two windings, namely the drive winding and the control winding which are configured as discrete coils and are wound about the long shank of the L-shaped coil cores. For this reason such a temple motor does without winding heads, so that e.g. the outlet of a pump housing can be arranged without spatial hindrance at the height of the fly wheel in the form of a radial outlet passage.

This design as a temple motor, e.g. in accordance with FIG. 12 of WO 96/31934 is, however, subjected, amongst other things, to the limitation that a relatively large spatial demand is present and is structurally demanding due to the high construction form.

For this reason a different rotational pump having a bearing-free motor is shown in EP 0 900 572 A1 of the applicant as an alternative to the temple motor which does without the constructionally relatively large and demanding temple motor.

In the meantime a series of embodiments having different arrangements and designs of the stator teeth are known, for example also those in which the stator teeth directly support the electric windings and lie substantially completely in the rotor plane which enables particularly compact constructional shapes.

In this respect it is frequently the case that in particular the rotor is an exchange part which, depending on the application has to be replaced more or less frequently. For example, because the rotor is operated for the pumping of mechanically or chemically very aggressive fluids or in very aggressive surroundings, for example, at increased temperature, so that the rotor wears relatively quickly and for this reason has to be replaced frequently.

Or, for example, on the treatment of sensitive or highly pure liquids, such as, for example, on the use in blood pumps or in bio-reactors, or for the handling of highly sensitive and/or highly pure fluids in the pharmaceutical and chemical industry, as well as generally in the medical field and in the field of medical technology it can be necessary, for example, for hygienic reasons and/or to prevent cross-contamination that the rotor has to be exchanged after one time use e.g. it is finally a disposable part.

The known rotors of the bearing-free disc-motors are in this respect in practice configured with a permanent magnet to stabilize the rotor, in particular with regard to tilting and/or an axial displacement with the aid of the above-described reluctance forces. Thereby the rotor becomes a very expensive exchange part and/or disposable part, as permanent magnets are comparatively expensive and the materials, such as e.g. rare earth materials have to be obtained at ever increasing prices from the market and with the prices continuously increasing. Apart from this, already for reasons of sustainability, it is not sensible to use very high quality and relatively rare materials which are required for the manufacture of permanent magnets as a disposable product. And even if the known rotors are redirected to reuse after use, so that the valuable materials are not or at least not completely lost, the manufacturing of rotors having permanent magnets is still very demanding in effort and cost and also the recycling is relatively complex and expensive.

For this reason it is an object of the invention starting from the prior art to provide a rotational machine, a rotor for a rotational machine as well as an apparatus having a rotational machine and/or having a rotor, wherein the rotor is cheap and simple in its manufacture and at the same time valuable resources can be saved and the rotor can be recycled sustainably and without large demand in effort and cost.

The subject matter of the invention satisfying this object are characterized by the independent claims of the respective category.

The dependent claims relate to particularly advantageous embodiments of the invention.

Thus, in accordance with the invention a rotational machine designed as a bearing-free motor is provided including a stator designed as a bearing and drive stator having a stator winding and a disc-shaped rotor stored magnetically contact-free within the stator. In this connection an axial height of the rotor is smaller than or equal to a half diameter of the rotor and the rotor is passively stabilized by reluctance forces with regard to the stator both against the displacement along a rotational axis of the rotor and also against a tilting from an equilibrium position, wherein the stator includes a permanent magnet for the generation of a homo-polar magnetic flux. In this respect the rotor is a ring-like rotor rotatably arranged about a pole piece of the stator and the rotor includes a ferromagnetic material and no permanent magnets.

As the rotor of the present invention does not include permanent magnets the rotor is now a very cheap exchange part and/or disposable part, as the rotor in accordance with the invention no longer includes rare earth materials and thus expensive materials, such as, for example, rare earths. Furthermore, the rotors in accordance with the invention can be recycled and reused after use without a great effort and without valuable materials being lost. Furthermore, the manufacture of rotors in accordance with the invention is significantly less demanding in effort and cost which leads to significantly reduced cost. Rotors in accordance with the invention can be manufactured simply from a ferromagnetic material, such as, for example, in the simplest case from iron, which, depending on the application, can possibly still be coated with a suitable material, for example with a plastic.

The use of rotors which include no permanent magnets becomes possible in accordance with the present invention, on the one hand, because a closed magnetic feedback is manufacturable via the pole piece, which is provided in a recess in the rotor which is provided about a rotational axis of the rotor, the stator and the rotor itself. For this reason, naturally beside the rotor, both the stator itself and also the pole piece of the stator must be manufactured at least from a ferromagnetic material, such as, for example, iron and/or at least be partially manufactured from a permanent magnetic material. In accordance with the invention at least one permanent magnet is provided at the stator and/or at the pole piece of the stator such that the rotor is flushed by a homo-polar magnetic flux, so that the rotor, as is known per se, is stabilized passively magnetically by reluctance forces with regard to three degrees of freedom, namely its axial displacement in the direction of the rotational axis and the tilting with regard to the plane perpendicular to the rotational axis (two degrees of freedom).

In this respect a closed magnetic flux is to be understood by a homo-polar flux which has its source in the permanent magnet provided at the stator or at the pole piece. In this respect each orthogonal component of the homo-polar flux resulting in the rotor towards the rotational axis is only directed in a single radial direction, namely with regard to the rotational axis either radially outwardly or radially inwardly in a direction of the rotational axis.

In a preferred embodiment, particularly relevant for practice, the permanent magnet is the pole piece or is provided at the pole piece and is polarized along its rotational axis. Thereby a corresponding homo-polar flux is induced which, starting from a magnetic pole of the permanent magnet, is closed via the rotor and the stator back to the other magnetic pole of the permanent magnet.

In this respect the permanent magnet can be provided in a circumferential direction of the stator and is additionally or in a different embodiment also alternatively polarized along its rotational axis and/or the permanent magnet can also additionally or alternatively be provided in a base region of the stator and be polarized in a radial direction orthogonal to the rotational axis.

Since the permanent magnet, as explained above, can in principle be provided at any suitable position outside of the rotor at the stator or at the pole piece, the permanent magnet can, alternatively or in addition to one variant or to a variant described in this application, also be provided in a cover region of the stator and can be polarized in a radial direction orthogonal to the rotational axis. Or, however, a permanent magnet can alternatively or additionally be provided in or at a stator tooth of the stator.

In this respect in principle any known rotational machine referred to, in the sense of this application, as bearing-free motors having a pole piece and a disc-shaped rotor can in principle be equipped with a rotor in accordance with the invention when only one permanent magnet is suitably provided outside the rotor at the stator or at the pole piece.

For example, a rotational machine in accordance with the invention can have a stator tooth designed L-shaped, wherein a shank of the stator tooth extends in parallel to the rotational axis and a different shank of the stator tooth extends radially to the rotational axis towards the rotor. In particular, a rotational machine in accordance with the invention can, for example, be designed in the form of a temple motor.

In a different preferred embodiment the stator teeth of a rotational machine in accordance with the invention can be designed completely in the plane of the rotor, so that the rotational machine has a very compact and space-saving construction form with regard to the axial direction.

So that a magnetic drive force can be exerted in the circumferential direction of the rotor, the distribution of the ferromagnetic material is naturally not allowed to be completely uniform in the rotor, but must be constructed in a suitable manner. For this reason the rotor can, for example, have an irregular outer contour having a rotor tooth directed radially outwardly.

Or, however, the rotor can have a circular outer contour, wherein the ferromagnetic material of the rotor is distributed according to a predefinable scheme with regard to a circumferential direction or with regard to a radial direction at or in the rotor. This principle is generally well known to a person of ordinary skill in the art under the term "synchronous reluctance motor".

In practice, a sensor unit having a sensor for the determination of a magnetic field strength is provided at the stator, in particular at the pole piece, so that a regulation of the position of the rotor orthogonal to the axis of rotation is possible in the operating state.

The active regulation of the position in each of the two radial directions of the rotor in this respect occurs preferably by means of at least one sensor for each direction attached at the stator circumference or at the pole piece, which measures the distance of the rotor to the stator. Alternatively it is possible, for reasons of improved linearity or resolution to also place two or more sensors for each direction, wherein the position in precisely this direction is determined, in a manner known per se to the person of ordinary skill in the art, by difference and/or sum formation depending on the placement of the sensors.

A movement of the rotor from the nominal position of the rotor into a specific direction, for example, by interfering influences, for example, leads to a decrease of the signal at the distance sensor which then leads to a deterioration of the field in the air gap precisely at this side and in turn this leads to an increase of the field at the opposite side by a correspondingly regulated current through-flowing and field producing coil. This causes a movement of the rotor in the direction to the nominal position and thus to an active radial stabilization. This type of regulation is generally known for bearing-free motors and does not have to be described further in detail.

In this respect the sensor is preferably a magnetic field sensor, in particular a Hall sensor, or a magnetoresistive sensor, or it can also be an eddy current sensor, and/or the sensor unit can also be formed by an array of a plurality of sensors.

The invention further relates to a disc-shaped rotor for a rotational machine in accordance with the invention, wherein in the framework of this application the term "disc-like rotor" is directed at a rotor whose axial height is smaller than or equal to its half diameter. It is thereby ensured that the rotor is stabilized simultaneously axially and against tilting alone by magnetic reluctance forces which act in the stator plane between the stator rotor and is thus purely passively stabilized. In this respect a rotor in accordance with the invention is a ring-like rotor having a recess provided about a rotational axis of the rotor in which in the inbuilt state the pole piece is receivable. In accordance with the invention, the rotor includes a ferromagnetic material and no permanent magnet.

Furthermore, the invention relates to an apparatus, in particular a wafer machining plant, a bio-reactor plant, a pump, a mixer or any different apparatus having a rotational machine and/or a rotor of the invention.

Figure 1B:
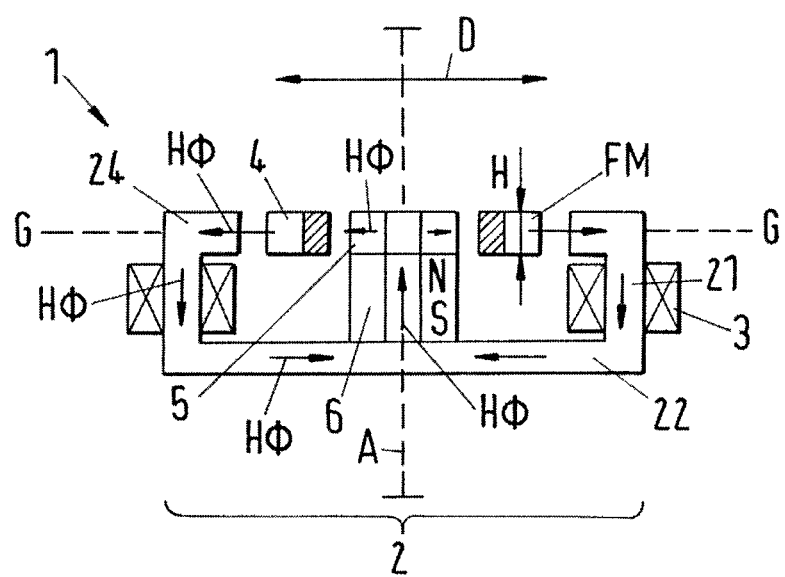
Figure 6B:
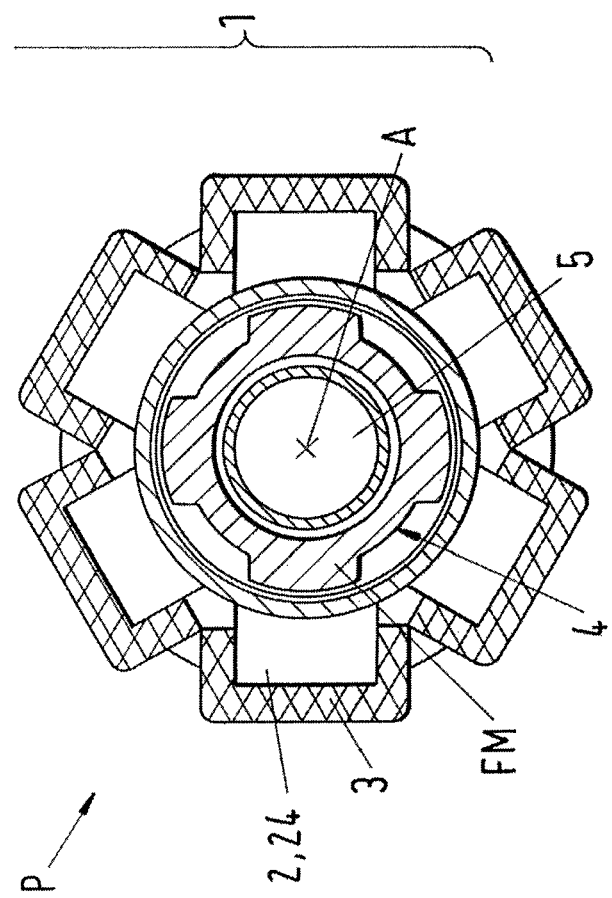

In the following the invention will be described in detail by means of embodiments with the aid of the drawing. The schematic drawing shows partially in section:

FIG. 1a a first embodiment of a rotational machine in accordance with the invention;

FIG. 1b a perpendicular section along the sectional line I-I in accordance with FIG. 1a;

FIG. 1c a horizontal section along the sectional line I-I in accordance with FIG. 1a for demonstrating the position regulation of the rotor in the X-direction;

FIG. 1d a horizontal section along the sectional line I-I in accordance with FIG. 1a for demonstrating the position regulation of the rotor in the Y-direction;

FIG. 2a a second embodiment of a rotational machine in accordance with the invention;

FIG. 2b a horizontal section along the sectional line II-II in accordance with FIG. 2a for demonstrating the position regulation of the rotor in the X-direction;

FIG. 2c a demonstration of the position regulation in accordance with FIG. 2a in the Y-direction;

FIG. 3 a third embodiment of a rotational machine in accordance with the invention having permanent magnets in the circumferential region;

FIG. 4 a fourth embodiment of a rotational machine in accordance with the invention having permanent magnets in the cover region;

FIG. 5a a first embodiment of a rotor having a circular outer contour;

FIG. 5b a different embodiment in accordance with FIG. 5a;

FIG. 5c a second embodiment of a rotor having a circular outer contour;

FIG. 5d a third embodiment of a rotor having a circular outer contour;

FIG. 6a a section through a pump in accordance with the invention;

FIG. 6b a horizontal section along the sectional line in accordance with FIG. 6a.

A first embodiment of a rotational machine in accordance with the invention is illustrated by means of the schematic drawing shown in FIG. 1a to FIG. 1d which in the following will be referred to overall with the reference numeral 1. In this respect FIG. 1b shows a perpendicular section along the sectional line I-I in accordance with FIG. 1a and FIG. 1c and FIG. 1d each respectively showing a horizontal section along the sectional line I-I in accordance with FIG. 1a for demonstrating the position regulation of the rotor in the X-direction or in the Y-direction in the X-Y-plane perpendicular to the axis of rotation of the rotor.

The rotational machine 1 in accordance with the invention according to FIG. 1 is designed as a bearing-free motor in a manner known per se, as has initially been described, including a stator 2 designed as a bearing and drive stator having a stator winding 3 and a disc-shaped rotor 4 stored within the stator 2 magnetically and contact-free. As has also already been mentioned a disc-shaped rotor in the framework of this application is a rotor whose axial height H is smaller than or equal to a half diameter D of the rotor 4.

In this respect the diameter D of the rotor 4 is defined as the maximum separation distance present at the rotor 4 between two outer lying boundaries of a ferromagnetic material provided at or in the rotor 4 with regard to a rotational axis A of the rotor. This will be described in the following in more detail by means of the drawing.

In this respect the rotor 4 is stabilized, as is common for bearing-free motors in the sense of this application, passively by reluctance forces with regard to the stator 2, both against a displacement along a rotational axis A and also against a tilting against the rotational axis A from an equilibrium position G and the stator 2 includes a permanent magnet 6 for the generation of a homo-polar magnetic flux HΦ. In accordance with the invention the rotor 4 is a ring-like rotor 4 rotatably arranged about a pole piece 5 of the stator 2 and the rotor 4 includes a ferromagnetic material FM and no permanent magnets.

As has already been explained in detail an essential characteristic of the bearing-free motor is that it has no separate magnetic bearings for the rotor 4. For this purpose, the stator 2 includes, in a suitable arrangement, a permanent magnet 6 and the rotor 4 includes a ferromagnetic material FM but no permanent magnets for realizing a passive magnetic storage.

In this respect the pole piece 5 is essential for the rotational machine 1 in accordance with the invention. The use of rotors 4 which include no permanent magnets becomes possible in accordance with the invention namely thereby that a closed magnetic feedback is manufacturable via the pole piece 5, which is provided in a recess at the rotor 4 which recess is provided about the rotational axis A of the rotor, the stator 2 and the rotor 4 itself. For this reason it is also expediently necessary that the rotor 4 is designed as a ring-like rotor 4 having the mentioned recess for the pole piece 5.

For this purpose naturally both the stator 2 and also the pole piece 5 of the stator must at least partially include a ferromagnetic material FM, such as for example iron and/or must at least be partially manufactured from a permanent magnetic material beside the rotor 4. For this reason at least one permanent magnetic material FM, i.e. a permanent magnet, is provided at the stator 2 and/or at the pole piece 5 of the stator, such that the rotor 4 is flushed by the homo-polar magnetic flux HΦ, so that the rotor 4 is stabilized passively magnetically by reluctance forces as known per se with regard to three degrees of freedom, namely an axial displacement in the direction of the rotational axis A and a tilting with regard to the X-Y-plane perpendicular to the rotational axis A (two degrees of freedom).

In this respect a homo-polar flux HΦ is to be understood as a closed permanent magnetic flux progress which has its source provided in the permanent magnet provided at the stator 2, in particular at the pole piece 5 as has already been mentioned in the introduction. In this respect each resulting orthogonal component of the homo-polar flux HΦ in one and the same motor is always only directed in one single radial direction in the rotor 4, namely with regard to the rotational axis A either only radially outwardly or radially inwardly in the direction of the rotational axis. It is naturally understood, that the homo-polar flux of a specific rotational machine 1 in accordance with the invention starting from the rotational axis A can be directed radially outwardly and for a different embodiment can be directed radially inwardly, which finally depends on the magnetic orientation i.e. the direction of polarization of the permanent magnet provided at the stator 2 or at the pole piece 5.

At this point it should be emphasized that the homo-polar flux HΦ generated by the permanent magnet should strictly be distinguished from the control flux HS which is generated by the stator windings 3 and is superimposed onto the homo-polar flux HΦ and which serves for the control and/or regulation of the radial position of the rotor 4 in the X-Y-plane which X-Y-plane is orientated perpendicular to the rotational axis A. The effect of the control flux HS will be explained in more detail later on in the discussion of FIG. 1c and FIG. 1d and/or of FIGS. 2b and 2c.

In the specific embodiment illustrated in FIG. 1a-FIG. 1d the permanent magnet 6 is provided at the pole piece 5 in accordance with the illustration below the pole piece 5 and is polarized along the rotational axis A.

The stator teeth 24 are formed at the stator 2 L-shaped so that a shank of the stator tooth 24 extends in parallel to the axis of rotation A and a different shank of the same stator tooth 24 extends radially to the rotational axis A towards the rotor 4.

In this respect the rotor 4 has an irregular outer contour 41 having a radially outwardly directed rotor 411, wherein the ferromagnetic material FM is provided at least in the rotor teeth 411, so that the ferromagnetic material FM of the rotor 4 is distributed in accordance with a predefinable scheme at least with regard to a circumferential direction U at or in the rotor 4, so that by means of a magnetic drive field generated by the stator winding 3 the rotor 4 can be placed into rotation about the rotational axis A.

A sensor device 7 having a sensor for the determination of a magnetic field strength is provided at the stator 2, in this example also at the pole piece 5 for the control and/or regulation of the radial position of the rotor 4 in the X-Y-plane, which can be seen in the sectional image in FIG. 2c and FIG. 2d, and which is orientated perpendicular to the rotational axis A, wherein a sensor device 7 can naturally also be provided, for example, only at the pole piece 5 or only at or only between the stator teeth 24 in a different embodiment. In this respect the sensor is preferably a magnetic field sensor, in particular a Hall sensor or is a magnetoresistive sensor or is an eddy current sensor, wherein the sensor device 7 can also be formed by an array 71 of sensors, as is, for example, also schematically illustrated in FIG. 1.

In this respect the stator 2 includes the electric stator winding 3, as mentioned, by means of which an electromagnetic rotary field is generatable which, on the one hand, exerts a torque onto the rotor 4 which, in the operating state, drives its rotation about the rotational axis A and which, on the other hand, exerts an arbitrarily settable transverse force onto the rotor 4 so that its radial position is predefinable and/or actively controllable or regulatable with regard to the X-Y-plane perpendicular to the axis of rotation A. Thereby the rotor 4 is actively controllable and/or drivable in the operating state by means of the electric stator windings 3 of the stator 2 with regard to three degrees of freedom, namely the rotation about the axis of rotation and also the radial position in the plane perpendicular to the axis of rotation (two degrees of freedom).

In the specific embodiment of a rotational machine 1 in accordance with the invention according to FIG. 1a to FIG. 1d a sensor device 7 in the form of four magnetic field sensors, for example Hall sensors or magnetoresistive sensors which measure the unipolar magnetic field can be recognized in detail at the polar piece 5. When the rotor 4, for example, is deflected to the right in accordance with the illustration, then the air gap on the right hand side between the pole piece 5 and the inner wall of the recess of the ferromagnetic ring rotor 4 increases and the air gap on the left side in accordance with the illustration between the pole piece 5 and the inner wall of the ferromagnetic rotor ring 4 is reduced. Thereby the magnetic field on the right hand side becomes smaller and the magnetic field on the left hand side becomes larger. The magnetic fields are measured by the right and left magnetic field sensors in accordance with the illustration and the difference of the signal between the left sensors and the right sensors forms a signal for the X-position (pointing to the right) of the rotor. In a similar manner also the Y-position can be determined from the forward and rear sensor signal.

The associated magnetic flux progress of the control flux HS are exemplary schematically illustrated for the control and/or regulation of the position of the rotor 4 for the X-direction in FIG. 1c and for the Y-direction in FIG. 1d. In this respect only one pair of flux lines HS has been respectively illustrated for reasons of clarity which respectively form a closed flux line of the control flux HS in the X-Y-Plane and which are superimposed onto the homo-polar magnetic flux HΦ, wherein the homo-polar magnetic flux HΦ can be seen particularly clearly in the perpendicular section of FIG. 1b perpendicular to the X-Y-plane over the pole piece 5 which is also closed. In this respect, the person of ordinary skill in the art also naturally understands that also other pairs of flux lines of the control flux HS could have been illustrated in FIG. 1c and FIG. 1d and that such further pairs of flux lines of the control flux HS are naturally also present in the operating state of the rotational machine 1.

It is naturally understood that instead of the magnetic field sensors in accordance with FIG. 1a and/or FIG. 1b also eddy current sensors could be advantageously used, wherein these are, for example, designed as conductive tracks of a rigid or flexible conducting plate.

In the particular embodiment in accordance with FIG. 1a arrangements of a plurality of magnetic field sensors which each form a magnetic field sensor array is provided in four of the intermediate spaces between neighboring stator teeth 24 in addition to the sensors at the pole piece 5. Such a magnetic field sensor array can be composed of a plurality of individual sensors or a plurality of individual sensors can, for example, be integrated onto a chip.

In dependence of whether a magnetic field sensor (in the magnetic field sensor array) is oppositely disposed of a rotor 411 (the illustrated rotor 4 has rotor teeth) or of a rotor groove (the illustrated rotor 4 also has four rotor grooves) the measured magnetic field is larger or smaller. From the signals of the individual magnetic field sensors the angular position of the rotor can thereby be determined. To compensate for oscillations which are brought about by the radial deflection of the rotor, the sum of 2×180° opposing sensors can preferably be formed. The sum is then generally independent from the oscillations of the radial position and practically only depends on the angular position of the rotor. Naturally also the radial position which was determined with the magnetic field sensors arranged inwardly can be used for compensating the radial position of the rotor 4. Thereby the demand for the hardware is smaller, however, the demand on the software side is slightly larger. Should the magnetic field signal be too small, additional radially magnetized magnet segments (magnetized in the same direction as the unipolar magnetic field) can be arranged behind the magnetic field sensor array. It is also possible to arrange small individual magnets behind the sensors. Naturally also an array of eddy current sensors can be arranged which, for example, are designed as conducting tracks of a rigid or flexible conducting plate instead of the magnetic field sensor.

FIGS. 2a to 2c show a second embodiment of a rotational machine 1 in accordance with the invention, wherein FIGS. 2b and 2c respectively show a horizontal section along the sectional line II-II in accordance with FIG. 2a for demonstrating a position regulation of the rotor. In the case of FIG. 2b the position regulation in the X-direction in the X-Y-plane perpendicular to the rotational axis and in the case of FIG. 2c the position regulation takes place with reference to two different pole pairs in accordance with FIG. 2a.

FIG. 2a shows a further embodiment of a rotational machine 1 in accordance with the invention which only differs from that in accordance with FIG. 1 in that a smaller number of stator teeth 24 are provided than in the example of FIG. 1. In this respect the stator teeth in accordance with FIG. 2a are arranged such that there is no rotor position in which each rotor tooth 411 faces a stator tooth 24 in contrast to the example of FIG. 1a in which the stator 2 settings of the rotor 4 result in which each rotor tooth 411 faces a stator tooth 24 due to the arrangement of the stator teeth 24.

This naturally has influences on the progress of the magnetic flux distribution of the control flux HS which is represented for the rotational machine of FIG. 2a exemplary in FIGS. 2b and 2c. In this respect, also for reasons of clarity only one pair of flux lines HS is respectively illustrated which each form a closed flux line of the control flux HS in the X-Y-plane and which are superimposed onto the homo-polar magnetic flux HΦ. Also in this example the person of ordinary skill in the art naturally understands that also other pairs of flux lines of control flux HS could just as well have been illustrated in FIG. 2b and FIG. 2c and that further pairs of flux lines of the control flux HS are also present in the operating state of the rotational machine 1.

It is generally clear that the invention is not restricted to rotational machines 1 having a certain number of stator teeth 24 and that an arbitrary number of odd and even numbers of stator teeth 24 is possible, wherein preferably at least three stator teeth 24 are present in practice. Naturally the shape of the rotor 4 is also in no way limited to the embodiments exemplary shown in the application and can in principle be configured arbitrarily provided a torque can be exerted onto the rotor 4 and it is magnetically stabilizable passively via reluctance forces.

With reference to FIG. 3 a third embodiment of a rotational machine 1 in accordance with the invention will be explained by way of example, in which the permanent magnet 6 is not provided at the pole piece 5, but in a circumferential region 21 of the stator 2 in the form of a ring magnet 6. This means, a ring-shaped permanent magnet 6 is provided in accordance with the illustration between an upper cover region 23 and a base region 22 of the stator 2 in this example which is polarized in the direction of the rotational axis A and thereby induces the homo-polar magnetic flux HΦ via the pole piece 5 and the rotor 4.

The person of ordinary skill in the art understands from the embodiment of FIG. 3 that e.g. also a plurality of individual permanent magnets 6 could be distributed over the circumference of the stator 2 instead of the ring magnet 6 which are polarized in the direction of the rotational axis A.

FIG. 4 shows a fourth embodiment of a rotational machine 1 in accordance with the invention, wherein the permanent magnet 6 designed in the form of a magnet ring 6 magnetically polarized in the radial direction in the cover region 23 of the stator 2, wherein, in a different embodiment, in a completely analogous manner the magnetic ring magnetically polarized in the radial direction and can also be designed alternatively or additionally in the base region 22 of the stator 2.

Also for these embodiments it is naturally possible that individual magnets 6 can be provided in the cover region 23 and/or in the base region 22 distributed over the circumferential direction U which are polarized perpendicular to the rotational axis A in radial direction instead of a radially magnetic polarized magnet ring 6 in the cover region 23 and/or in the base region 22 of the stator 2.

A particular advantage of the embodiments of FIGS. 3 and 4 lies therein that, amongst other things, the stator teeth 24 are completely arranged in the X-Y-plane of the rotor 4, i.e. are not L-shaped, which allows a particularly compact construction height with regard to the direction of the rotational axis A. In this respect it is in principle naturally also possible that also the embodiments, for example in accordance with FIG. 1*a* or FIG. 2*a* in which the permanent magnet 6 has been designed at the pole piece 5 are realizable by means of stator teeth 24 which are designed completely in the X-Y-plane of the rotor 4 such as in FIGS. 3 and 4.

It is also clear that the permanent magnets 6 can in principle be provided everywhere at the stator, i.e. also for example at the stator teeth 24, and that all possible embodiments can also be combined, for example, to set the strength of the homo-polar flux HΦ to a predeterminable strength.

A few other alternative variants of rotors 4 in accordance with the invention having a circular outer contour 42 are described by way of example with reference to FIGS. 5*a* to 5*d*.

The ring rotor 4 is carried out ring-shaped both at the inner recess and also at the outer contour 42 in the rotors 4 in accordance with FIGS. 5*a* to 5*d*.

In the example of FIG. 5*a* the rotor 4 is only composed of a ferromagnetic material FM in the kidney-shaped regions referred to with FM and is otherwise composed of a different material, for example, of a plastic.

For the most cases, however, in practice, embodiments in accordance with FIG. 5*b* to FIG. 5*d* are selected in which the magnetic anisotropy of the rotor 4 is thereby achieved that magnetic flux locks SP are introduced into the rotor 4. The flux locks SP are, for example, "recesses" in the form of slits or locking surfaces in the otherwise ferromagnetic structure FM of the rotor 4 which are filled with air or another non-ferromagnetic material, for example plastic. Since the magnetic flux through the non-ferromagnetic material experiences a very high magnetic resistance while the ferromagnetic material FM can be considered to be a "magnetic conductor" an arbitrary (2p-polar) anisotropy can be forced onto the rotor 4 through a suitable dimensioning of these flux locks SP. In particular the flux guiding can be optimized for the requirements, both with regard to the drive and also with regard to the magnetic storage by means of such flux locks SP. Thus, for example, an eventually possible so-called clogging can take place, as a person of ordinary skill in the art knows, for example in the rotor 4 shown in FIG. 1 (cross-shaped) is strongly reduced. It is also principally possible to realize 4-pol rotors 4 which are ideal both with regard to the drive and also with regard to the passive magnetic stabilization of the tilting and the axial position of the rotor 4 and also from the actively magnetic stabilization of the radial position of the rotor 4.

FIGS. 6*a* and 6*b* finally show an embodiment particularly important for practice of a rotational machine 1 in accordance with the invention in the form of a pump, for example, a centrifugal pump, wherein FIG. 6*b* shows a horizontal section along the sectional line III-III in accordance with the sectional drawing of FIG. 6*a* of the pump P.

The pump P in accordance with FIG. 6*a* and/or FIG. 6*b* has a rotational machine 1 with L-shaped stator teeth 24 as a drive, as was explained, for example, with reference to FIG. 1*a* or FIG. 2*a*. The permanent magnet 6 lies centrally at the polar piece 5 in this example. It is naturally understood that also other variants are possible with all different rotational machines in accordance with the invention.

Thus, as can be clearly recognized the pump housing PG with the rotor 4 arranged therein, which housing has an inlet and an outlet for a fluid to be pumped in a manner known per se, can be completely separated from the stator part at approximately the height of the sectional line III-III. In this respect the pump housing PG, apart from the inlet and outlet, is hermetically sealed against the environment and in particular also against the stator 2. When the rotor 4 must be exchanged, the pump housing PG can be lifted from the stator 2 and can be opened and a new rotor can simply be inserted. Naturally the pump as a whole can also be thrown away, i.e. is disposable and/or is designed as a single-use part.

The invention claimed is:

1. A rotational machine, designed as a bearing free motor, including a stator (2) designed as a bearing and drive stator having a stator winding (3) and a disc-shaped rotor (4) stored magnetically contact free within the stator (2), wherein an axial height (H) of the rotor (4) is smaller than or equal to a half diameter (D) of the rotor (4) and with the rotor (4) being passively stabilized by reluctance forces with regard to the stator (2) both against a displacement along a rotational axis (A) of the rotor (4) and also against a tilting from an equilibrium position (G), and with the stator (2) including a permanent magnet (6) for the generation of a homopolar magnetic flux (HΦ), wherein the rotor (4) is a ring-like rotor (4) rotatably arranged to surround a region of a coilless static pole piece (5) of the stator (2), wherein the ring-like rotor (4) is positioned during operation radially distant from and perpendicular to a longitudinal axis of the coilless static pole piece (5), wherein the coilless static pole piece (5) is configured for guiding the homopolar flux (HΦ) radially between the stator (2) and the rotor (4), and wherein the rotor (4) includes a ferromagnetic material (FM) and no permanent magnet.

2. A rotational machine in accordance with claim 1, wherein the permanent magnet (6) is the coilless static pole piece (5) or is provided at the coilless static pole piece (5) and is polarized along the rotational axis (A).

3. A rotational machine in accordance with claim 1, wherein the permanent magnet (6) is provided in a circumferential region (21) of the stator (2) and is polarized along the rotational axis (A).

4. A rotational machine in accordance with claim 1, wherein the permanent magnet (6) is provided in a base region (22) of the stator (2) and is polarized in a radial direction orthogonal to the rotational axis (A).

5. A rotational machine in accordance with claim 1, wherein the permanent magnet (6) is provided in a cover region (23) of the stator (2) and is polarized in a radial direction orthogonal to the rotational axis (A).

6. A rotational machine in accordance with claim 1, wherein the permanent magnet (6) is provided in or at a stator tooth (24) of the stator (2).

7. A rotational machine in accordance with claim 1, wherein the stator tooth (24) is designed L-shaped and a shank of the stator tooth (24) extends in parallel to the rotational axis (A) and a different shank of the stator tooth (24) extends radially to the rotational axis (A) towards the rotor (4).

8. A rotational machine in accordance with claim 1, wherein the rotor (4) has an irregular outer contour (41) having a rotor tooth (411) directed radially outwardly.

9. A rotational machine in accordance with claim 1, wherein the rotor (4) has a circular outer contour (42).

10. A rotational machine in accordance with claim 1, wherein the ferromagnetic material (FM) of the rotor (4) is distributed at or in the rotor (4) according to a predefinable scheme with regard to a circumferential direction (U) or with regard to a radial direction.

11. A rotational machine in accordance with claim 1, wherein a sensor device (7) having a sensor for the determination of a magnetic field strength is provided at the stator (2), specifically at the coilless static pole piece (5).

12. A rotational machine in accordance with claim 11, wherein the sensor is a magnetic field sensor, in particular a Hall sensor, or a magneto resistive sensor, or an eddy current sensor.

13. A rotational machine in accordance with claim 11, wherein the sensor device (7) is formed by an array (71) of sensors, in particular for the detection of an angular position of the rotor (4), and with the array being arranged at the stator (2).

14. A rotational machine in accordance with claim 11, wherein the sensor is a magneto resistive sensor.

15. A disc-shaped rotor for a rotational machine (1) in accordance with claim 1, wherein an axial height (H) of the rotor is smaller than or equal to a half diameter (D) of the rotor, and the rotor is a ring-like rotor having a recess provided about a rotational axis (A) of the rotor, wherein the rotor includes a ferromagnetic material (FM) and no permanent magnet.

16. An apparatus, in particular a wafer machining plant, a bioreactor plant, a pump (P), a mixer or a different apparatus having a rotor (4) in accordance with claim 15.

17. An apparatus, in particular a wafer machining plant, a bioreactor plant, a pump (P), a mixer or a different apparatus having a rotational machine (1) in accordance with claim 1.

* * * * *